(12) United States Patent
Ueno

(10) Patent No.: US 6,248,759 B1
(45) Date of Patent: Jun. 19, 2001

(54) METHOD FOR TREATMENT OF LIGHT-INJURED RETINAL DEGENERATION DISEASE

(75) Inventor: Ryuji Ueno, Montgomery, MD (US)

(73) Assignee: R-Tech Ueno, Ltd., Osaka-Fu (JP)

( * ) Notice: Subject to any disclaimer, the term of this patent is extended or adjusted under 35 U.S.C. 154(b) by 0 days.

(21) Appl. No.: 09/408,562

(22) Filed: Sep. 30, 1999

Related U.S. Application Data

(60) Provisional application No. 60/110,700, filed on Dec. 3, 1998, and provisional application No. 60/102,972, filed on Oct. 2, 1998.

(51) Int. Cl.$^7$ .................................................. A61K 31/44
(52) U.S. Cl. .................................... 514/340; 514/344
(58) Field of Search ...................................... 514/340, 344

(56) References Cited

U.S. PATENT DOCUMENTS 5,691,360   11/1997   Hellberg et al. .

FOREIGN PATENT DOCUMENTS

| 0 911 027 A1 | 4/1999 | (EP) | A61K/31/455 |
|---|---|---|---|
| 2 585 574 | 2/1987 | (FR) . | |
| 2 642 307 | 8/1990 | (FR) . | |
| 10-72347 | 3/1998 | (JP) | A61K/31/455 |
| 90 06123 | 6/1990 | (WO) . | |
| 97 40834 | 11/1997 | (WO) . | |

OTHER PUBLICATIONS

Young, R. W.; Surv. Ophthalmol., 32:252–269; 1998.
Yasuo Hosobe, J Jpn Ophthalmol Soc 100:665–671 (1996).
Jaffe, G. J. et al; Ophthalmology, 95:1130–1141; 1988.
Li, J. et al; Research Communications in Chemical Pathology and Pharmacology, 72:347–352; 1991.

I Sahly et al: "Calcium channel blockers inhibit retinal degeneration in the retinal–degeneration–B mutant of Drosophila", Jan. 1992, vol. 89, No. 1, pp. 435–439.

D P Edward et al: "Amelioration of Light–Induced Retinal Degeneration by a Calcium Overload Blocker", Apr. 1991, vol. 109, No. 4, pp. 554–562.

Database WPI, Derwent Publications Ltd., London, "Calcium Ion Inhibiting Hypertensive Agent: Nivaldipine", JP 04 128228 A, 1990, Abstract XP–002130585.

Li J P et al: "Nimodipine, a voltage–sensitive calcium channel antagonist, fails to ameliorate light–induced retinal degeneration in rat.", Jun., 1991, Research Communications in Chemical Pathology and Pharmacology, 72 (3) 347–52.

Vieira, W. et al: "Intravitreal calcium channel blockers in retinal degeneration in the trasgenic mouse.", IOVS, Mar. 15, 1998, vol. 39, No. 4, pp. S277 XP–000879195, abstract.

Database Biosis, Govardovskii V. I. et al, "Light–Induced Calcium Release from Retinal Photoreceptors and Calcium Hypothesis of Visual Excitation.", Abstract XP–002130584, 1987.

*Primary Examiner*—Rebecca Cook
(74) *Attorney, Agent, or Firm*—Sughrue, Mion, Zinn, Macpeak & Seas, PLLC

(57) ABSTRACT

A method for treatment of light-injured retinal degeneration disease comprising, administering an effective amount of a dihydropyridine calcium antagonist other than nimodipine is provided. The dihydropyridine calcium antagonist used in the present invention is useful for treatment of light-injured retinal degeneration, especially macula lutea degeneration including age-related macula degeneration.

10 Claims, No Drawings

METHOD FOR TREATMENT OF LIGHT-INJURED RETINAL DEGENERATION DISEASE

CROSS REFERENCE TO RELATED APPLICATIONS

This application is an application filed under 35 U.S.C. §111(a) claiming benefit pursuant to 35 U.S.C. §119(e)(1) of the filing date of the Provisional Application No. 60/102,972, filed Oct. 2, 1998, and Provisional Application No. 60/110,700, filed Dec. 3, 1998 pursuant to 35 U.S.C. §111(b).

BACKGROUND OF THE INVENTION

1. Field of the Invention

The present invention relates to a method for treatment of light-injured retinal degeneration disease.

2. Related Arts

In the structure of eye, the retina exists at the ocular fundus and takes charge of the function of eye, which recognizes the presence or absence, and the shape of things in virtue of the existence of the neuroepithelial layer in the retina. In addition, the central portion of the retina is called macula lutea and one can distinguish things and feel colors by the action of the macula lutea.

The retina is destined to chronic exposure to light throughout the life. Particularly, the macula lutea, the central and most vital area of the retina, is likely to be damaged by light than the peripheral region of the retina. It has been pointed out that damage to the retina resulting from light exposure is accumulative and that the damage may promote age-related changes of retina which induce age-related macular degeneration or the like (Young, R. W.; Surv. Ophthalmol., 32: 252–269; 1988, the disclosures of which are herein incorporated by reference). It has also been described that light exposure may cause pathological conditions similar to that of age-related macular degeneration, i. e., a formation of drusen, neovascularization originated from choroidal membrane and the like. Statistically, age-related macular degeneration patients have been reported to be less likely cataract patients and more likely out-door laborers or habitants in UV-rich area.

The age-related macular degeneration is classified into the non-leakage type (dry type), which is simply called as age-related macular degeneration, and the exudative type, which is called as age-related disciform macular degeneration. In the dry type, drusen and atrophy of pigment epithelium may be observed in the macula lutea, and the vision may be damaged significantly. In the exudative type, new blood vessels originated from the choroidal membrane may develop in the macula lutea under the retina membrane, which resulting in hemorrhage, exudation and cicatrization, and further, in degeneration of the macula lutea. In the progressed stage, the visual loss becomes advanced and irreversible. At present, no effective treatment is available for the dry (non-leakage) type age-related macular degeneration. For the exudative type, it has been said that the only treatment, which might be effective, is laser photocoagulation. Recently, the effect of interferon for treatment of the exudative type was studied, but this could not necessarily be said as effective because of its side effects.

The calcium antagonists inhibit inflow of calcium ions into the vascular smooth muscle cells thereby relax the muscle to dilate the peripheral blood vessel, and thereby decrease the vascular resistance and increase the blood circulation. Clinically, they are used not only as hypotensive drugs but also as cerebral vasodilators.

In addition, in the ophthalmic field, the calcium antagonists have been attempted to use for treatment of low-tension glaucoma and it was reported that improvement of the visual field was observed in some cases. It has also been reported that the calcium antagonists increase the blood circulation in choroid, retina and optic disc (See WO97/40834, the disclosures of which are herein incorporated by reference). Based on the above actions, some calcium antagonists, for example dihydropyridine calcium antagonists such as nicardipine and pranidipine, have been concluded to be effective for treatment of ischemia-reperfusion disorder of retina (see Yasuo Hosobe, J Jpn Ophthalmol Soc 100: 665–671 (1996), and Japanese Patent Laid Open No. 10/72347, the disclosures of each of which are herein incorporated by reference).

Any efficacy of the calcium antagonists on the light-injured retinal degeneration disease, however, can not be expected from these publications. Increase in blood flow in ocular tissues such as choroid results in increase in oxygen feed to the neuroepithelial layer. It has been known, however, that light-induced retinal disorder is promoted under such condition (Jaffe, G. J. et al; Ophthalmology, 95: 1130–1141; 1988, the disclosures of which are herein incorporated by reference). It has also been described that Nimodipine, one of the dihydropyridine calcium antagonists, was not effective to light-induced retinal disorder (Li, J. et al; Research Communication in Chemical Pathology and Pharmacology, 72: 347–352; 1991, the disclosures of which are herein incorporated by reference).

SUMMARY OF THE INVENTION

After conducting extensive studies, the present inventor has surprisingly found the fact that the dihydropyridine calcium antagonists other than nimodipine have an excellent improving action on the light-induced retinal disorder and have an excellent therapeutic effect on the light-injured retinal degeneration disease. The present invention has been completed based upon such findings.

Accordingly, the present invention provides a method for treatment of light-injured retinal degeneration disease comprising administering an effective amount of a dihydropyridine calcium antagonist other than nimodipine to a subject in need of such treatment. Preferably, the dihydropyridine calcium antagonist may be a compound of the formula (I):
wherein, $R_1$ is a halogen atom or a nitro group;

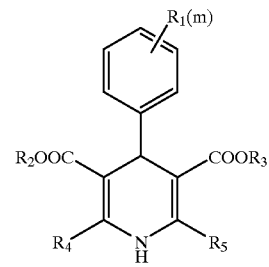

(I)

m is a number of 1 or 2;
$R_2$ is a lower alkyl group;
$R_3$ is a lower alkyl group or a group represented as
—A—X
wherein
A is a saturated or unsaturated hydrocarbon residue having 2–6 carbon atoms;

X is

<chemical structure>

$R_4$ is a lower alkyl group; and $R_5$ is a lower alkyl, cyano or amino lower alkoxy lower alkyl group or a pharmaceutically acceptable salt thereof.

More preferably, the compound of the formula (I) may be of the formula (II):

<chemical structure (II)> wherein each of $R_2'$, $R_3'$ and $R_4'$ represents lower alkyl group respectively or a pharmaceutically acceptable salt thereof, and most preferably, the compound is nilvadipine.

According to the present invention, the method is useful for treatment of retinal degeneration, especially degeneration in macula lutea including age-related macular degeneration.

DETAILED DESCRIPTION OF THE INVENTION

The calcium antagonist used in the present invention is not particularly limited insofar as it belongs to dihydropyridine calcium antagonists other than nimodipine. Specific examples include, without limitation, nilvadipine, nicardipine, nitrendipine, nifedipine, felodipine, nisoldipine, iganidipine, amlodipine, pranidipine and pharmacologically acceptable salts thereof Examples of preferred dihydropyridine calcium antagonists include compound of the following formula (I):

<chemical structure (I)> wherein $R_1$ is a halogen atom or a nitro group;

m is a number of 1 or 2;

$R_2$ is a lower alkyl group;

$R_3$ is a lower alkyl group or a group represented by —A—X wherein

A is a saturated or unsaturated hydrocarbon residue having 2–6 carbon atoms;

X is

<chemical structure>

$R_4$ is a lower alkyl group, $R_5$ is a lower alkyl, cyano, or amino lower alkoxy lower alkyl group, or a pharmaceutically acceptable salt thereof.

The definitions of the terms used in the present invention are as follows:

The term "halogen" includes fluorine, chlorine, bromine, and iodine.

The term "lower alkyl" means a straight or branched-chain of saturated hydrocarbon group having 1 to 6 carbon atoms which include, for example, methyl, ethyl, propyl, isopropyl, butyl, isobutyl, t-butyl, pentyl, and hexyl.

The term "saturated or unsaturated hydrocarbon residue having 2–6 carbon atoms" means a straight or branched-chain of C2–C6 hydrocarbon residue which is saturated or has at least one double and/or triple bonds, for example, ethylene, propylene, butylene, 2-methyl-propylene, 2-methyl-butylene, 2,2-dimethyl-propylene, vinylene, 1-propenylene, 2-methyl-1-propenylene, 1-butenylene, 1,3-pentadienylene.

The term "lower alkoxy" means a lower alkyl-O— wherein the lower alkyl is as described above.

The term "amino lower alkoxy lower alkyl group" means a lower alkyl group having an alkoxy group which comprises at least one amino group, for example, aminomethoxy methyl, 2-aminoethoxy methyl, 3-amino propoxyethyl, and 3,3-diamino propoxy ethyl.

Examples of suitable "pharmaceutically acceptable salts" include nontoxic salts which are commonly used in the pharmaceutical field, for example, salts of organic acid, such as acetate, trifluoro acetate, maleate, tartarate, methane sulfonate, benzene sulfonate, formate, or toluene sulfonate; salts of inorganic acid, such as hydrochloride, hydrobromide, hydroiodide, sulfate, nitrate and phosphate; and salts of acidic amino acid such as aspartate and glutamate.

According to the present invention, especially preferable compounds are of the following formula (II):

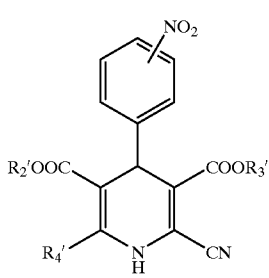

(II)

wherein each of $R_2'$, $R_3'$ and $R_4'$ is lower alkyl group respectively, and a pharmaceutically acceptable salts thereof.

The most preferable compound of the formula (II) is that the 3rd position of the benzene ring is substituted with a nitro group, $R_2'$ is isopropyl, and both of $R_3'$ and $R_4'$ are methyl groups. Namely, the compound of the formula:

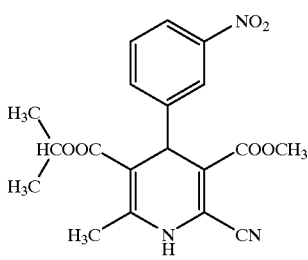

(III)

i.e. 5-isopropyl-3-methyl-2-cyano-1,4-dihydro-6-methyl-4-(m-nitrophenyl)-3,5-pyridinedicarboxylate of which common name is nilvadipine.

The dihydropyridine calcium antagonist used in the present invention is useful as therapeutics for human and animals and may be given systemically or locally through oral administration, intravenous administration (including drip), subcutaneous administration, rectal and intravaginal administration, ocular local administration and the like.

The effective amount of the dihydropyridine calcium antagonist to be administered varies depending on the species, age, weight, sex, and general condition of the subject to be treated, symptom to be treated, desired effect of the therapy, way of administration, duration of treatment and the like, and it may be determined by an ordinary skilled person in this art field. Typically a daily dose of about 0.001–100 mg/kg may be given by dividing it into 2–4 times a day or by means of a sustained release composition for systemic administration. According to the present invention, the dihydropyridine calcium antagonist may be administrated as a composition, which is formulated in an appropriate dosage form, comprising the same as an active ingredient.

Solid composition for oral administration according to the present invention includes tablets, troches, sublingual tablets, capsules, pills, powders, granules and the like. In these solid compositions, one or more active substances may be mixed with at least one inactive diluent. The composition may further contain a lubricant, disintegrator and stabilizer, which are used in a conventional solid pharmaceutical composition. The tablets or pills may either be coated with a gastric or enteric film or coated with two or more layers. Liquid composition for oral administration includes solution, emulsion, suspension, syrup, elixir and the like. Commonly used inactive diluent, for example, purified water, ethanol and so on, may also be added. The composition may further contain adjuvant, such as humectant and suspending agent, sweetener, flavor, perfume, preservative and the like.

Injectable composition for the parenteral administration according to the present invention includes sterile aqueous or non-aqueous solution, suspension, emulsion and the like. Examples of the aqueous vehicle include distilled water for injection, physiological saline, Ringer's solution and the like. Examples of the non-aqueous vehicle include vegetable oils, ethanol and the like. The injectable composition may further contain adjuvant such as preservative, humectant, emulsifying agent, dispersing agent and so on. The composition may be sterilized by, for example, filtration through a bacterial filter, inclusion of a sterilizing agent, gas sterilization, radiation and the like. The injectable composition may also be provided as a sterile solid composition, which is to be dissolved in a sterile vehicle for injection before use.

Composition for rectal or intravaginal administration includes suppository and vaginal suppository. The composition may be prepared by mixing the active ingredient with a base, which softens at the body temperature.

Composition for ocular local administration includes eye drop and eye ointment. The eye drop may be prepared by dissolving or suspending the active ingredient in a sterile vehicle, or may be provided as a sterile solid composition, which is to be dissolved in the sterile vehicle before use. The eye ointment may be prepared by mixing the active ingredient with an appropriate base.

According to the present invention, the composition may further contain any other ingredient having a desired pharmaceutical activity insofar as it does not adversely affect the purpose of the present invention.

The dihydropyridine calcium antagonist shows a direct improving activity on injured retinal visual cells as demonstrated in the animal model of which retinal visual cells are injured by strong light radiation (see Test Examples below). This findings strongly support that the dihydropyridine calcium antagonist is effective for treatment of light-injured degenerative diseases such as retinal degeneration and/or degeneration of macula lutea. Because the macula lutea is the region where being always exposed to light, and therefore, is more likely being damaged by light than the peripheral area of the retina and light exposure damages retina accumulatively, once developed degeneration of the macula lutea, irrespective of the etiology, including atrophy or edema, might be further progressed by further light exposure. The dihydropyridine calcium antagonist may also be useful for treatment of such accumulatively injured retina including macula lutea, and especially for treatment of age-related macular degeneration, which has recently been the subject of growing interest but no effective treatment has not yet been known. In addition, bright light radiation in an ophthalmic operation, such as vitrectomy, may sometimes cause degeneration of the macula lutea, and the method of the present invention may also be useful for treatment of the degeneration by administering before or after the opthalmic operation.

In the method of the present invention, the composition as described above is administered to a subject in need of treatment for light-injured retinal degeneration disease.

The term treatment used in the present invention includes all kinds of control, such as prophylaxis, cure, relief of symptoms, attenuation of symptoms, arrest of advance and the like According to the present invention, a subject in need of treatment for light-injured retinal degeneration disease includes not only a subject, which may be a human or an animal, and has already been suffering from a light-injured retinal degeneration disease, but also a subject which is susceptible to be suffered from such conditions as described above including, for example, an elder person, a person with diabetes, an inhabitant in an UV-rich area, and who is receiving ophthalmic surgery.

The present invention will now be described below in more detail with reference of Example, which should not be construed as a limitation upon the present invention.

EXAMPLES

Test Example 1 (Light-injured Model of Rat Retinal Visual Cells)

(1) Test substance and its preparation

Nilvadipine (2 mg Nivadil™ Tablets, manufactured by Fujisawa Pharmaceutical Co., Ltd.) was pulverized in an agate mortar to give powders. The powders were treated by gradual addition of a physiological saline containing 0.5% sodium carboxymethylcellulose so that they were homogeneously dispersed in an aqueous solution to give a suspension containing 20 µg/ml of Nilvadipine.

(2) Test animals and preparation of model animals

Male SD rats (9 weeks of age, 280–330 g) were subjected to a quarantine-acclimatization period of one week and allotted to groups on the last day before the commencement of continuous light irradiation. The rats were individually housed in cages.

Light sources were placed so that the cages obtained an illuminance of 1,000 Luxes from every direction. Rats received three times of 24-hours continuous light irradiation (from 9:00 to 9:00 on the next day) every other day (day 1, day 3 and day 5).

(3) Administration of test substance

On day 2, day 4 and days 6–12 on which the 24-hours continuous light irradiation was not carried out, the rats were transferred to a rearing house set to alternate 12 hours light and dark periods (illumination with fluorescent lamps, about 70 Luxes in the light period) and received subcutaneous administration of test substance 4 times a day (9:00, 12:00, 15:00 and 18:00). Disease control group received subcutaneous administration of the same amount of vehicle alone. Normal control group was kept in a rearing house set to alternate 12 hours light and dark periods (illumination with fluorescent lamps, about 70 Luxes in the light period).

(4) Preparation of specimen

On the day after the completion of the administration of the test substance (day 13), the rats were sacrificed by ether over-anesthesia. Both eyeglobes were isolated and immediately immersed in a fixative (a phosphate buffer solution containing 2% formaldehyde and 2.5% glutaraldehyde). After 2.5 hours, corneas were excised with a razor and the globes lacking lenses were immersed overnight in the same fixative. The fixed ophthalmic tissue was dehydrated with a series of alcohol (70–100% ethanol), embedded in paraffin and an area around the optic disc was sliced parallel along the meridian of the eyeglobe with a sliding type microtome. On the next day, the obtained slices were subjected to hematoxylin-eosin staining. In this manner, three retinal tissue specimens per an eye were prepared containing optic disc area.

(5) Measurement of thickness of cell layer

The specimen was examined at a magnification of 100 diameter with an optical microscope. A microphotograph was taken on a positive film (RAP 135, manufactured by Fujifilm). The thickness of the outer nuclear layer was measured in a projected picture and the measurement was repeated on three specimens per eye. Averages were calculated from the obtained values per eye.

(6) Results

| Test group | Amount of administration (mg/kg) | n (eyes) | Thickness (µm) of outer nuclear layer (mean ± standard deviation) |
|---|---|---|---|
| 1 Normal control (untreated) | — | 10 | 48.6 ± 5.3 |
| 2 Disease control | vehicle | 10 | 29.9 ± 6.6## |
| 3 Nilvadipine | 0.1 | 10 | 25.0 ± 5.4 |
| 4 Nilvadipine | 1.0 | 10 | 36.9 ± 5.2* |

: $P < 0.01$ (Comparison with the normal control group by Student's T-test)
*: $P < 0.05$ (Comparison with the disease control group by Dunnett test)

The thickness of the outer nuclear layer in the disease control group was significantly lower than that of the normal control group, indicating that the outer nuclear layer of the rat retina became thinner by the light irradiation.

The administration of Nilvadipine increased dose-dependently the thickness of the outer nuclear layer and the thickness of the outer nuclear layer in the 1.0 mg/kg administration group was significantly greater than that of the disease control group, demonstrating a clear inhibiting effect on the light-induced retinal degeneration.

What is claimed is:

1. A method for treatment of light injured retinal degeneration disease which comprises administering an effective amount of dihydropyridine calcium antagonist other than nimodipine to a subject in need of said treatment.

2. The method according to claim 1, wherein the dihydropyridine calcium antagonist is the compound of the formula (I):

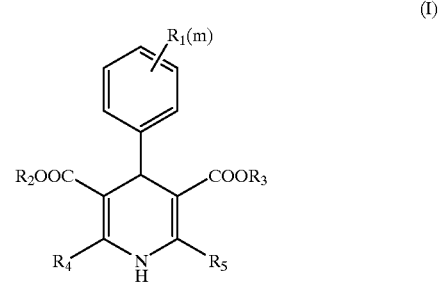

(I)

wherein, $R_1$ is a halogen atom or a nitro group;

m is a number of 1 or 2;

$R_2$ is a lower alkyl group;

$R_3$ is a lower alkyl group or a group represented as —A—X wherein

A is a saturated or unsaturated hydrocarbon residue having 2–6 carbon atoms;

X is

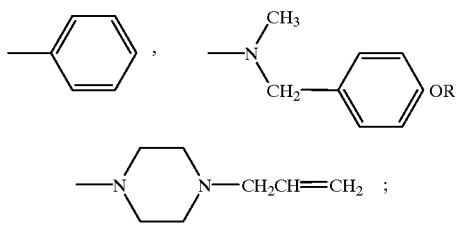

$R_4$ is a lower alkyl group; and $R_5$ is a lower alkyl, cyano or amino lower alkoxy lower alkyl group or a pharmaceutically acceptable salt thereof.

3. The method according to claim 2, wherein the compound is of the formula (II):

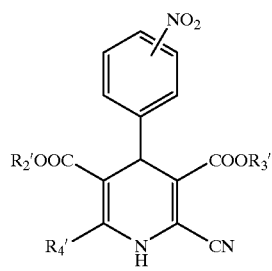

(II)

wherein each of $R_2'$, $R_3'$ and $R_4'$ is lower alkyl group respectively or a pharmaceutically acceptable salt thereof.

4. The method according to claim 3, wherein the dihydropyridine calcium antagonist is nilvadipine.

5. The method according to claim 1, wherein the retinal degeneration is degeneration of the macula lutea.

6. The method according to claim 1, wherein the retinal degeneration is age-related retinal degeneration.

7. The method according to claim 5, wherein the retinal degeneration is age related macula degeneration.

8. The method according to claim 1, wherein the effective amount is daily dose of about 0.001–100 mg/kg of the body weight of the subject.

9. A method for treatment of damage of the retina resulting from light exposure, which comprises administering an effective amount of a dihydropyridine calcium antagonist other than nimodipine to a subject in need of said treatment.

10. A method for protecting retinal visual cells from damage occurring from light exposure, which comprises administering an effective amount of a dihydropyridine calcium antagonist other than nimodipine to a subject in need of said protection.

* * * * *